(12) United States Patent
Kudoh et al.

(10) Patent No.: US 6,762,277 B2
(45) Date of Patent: Jul. 13, 2004

(54) METHOD OF MANUFACTURING N-CARBOXYAMINO ACID ANHYDRIDE AND POLYAMINO ACID

(75) Inventors: Hiroto Kudoh, Yokohama (JP); Takeshi Endoh, Yokohama (JP)

(73) Assignee: JSR Corporation, Tokyo (JP)

( * ) Notice: Subject to any disclaimer, the term of this patent is extended or adjusted under 35 U.S.C. 154(b) by 0 days.

(21) Appl. No.: 10/132,468

(22) Filed: Apr. 26, 2002

(65) Prior Publication Data

US 2002/0188095 A1 Dec. 12, 2002

(30) Foreign Application Priority Data

Apr. 27, 2001 (JP) ........................... 2001/132055

(51) Int. Cl.[7] ................ C08G 73/00; C08G 69/00; C07D 263/44
(52) U.S. Cl. ................. 528/328; 528/170; 528/183; 528/184; 528/189; 528/196; 528/206; 528/208; 528/310; 528/342; 548/227; 548/577; 525/411
(58) Field of Search ................. 528/328, 170, 528/183, 184, 189, 196, 310, 206, 208, 342; 548/227, 577; 525/411

(56) References Cited

U.S. PATENT DOCUMENTS

| | | | | |
|---|---|---|---|---|
| 4,033,997 A | * | 7/1977 | Roteman | 558/269 |
| 5,852,109 A | * | 12/1998 | Makino et al. | 524/811 |
| 5,854,384 A | * | 12/1998 | Kuroda et al. | 528/355 |

FOREIGN PATENT DOCUMENTS

| JP | 63 035596 | * | 2/1988 |
|---|---|---|---|
| JP | 1988 112565 | * | 5/1988 |
| JP | 1988 122659 | * | 5/1988 |
| JP | 03 095223 | * | 4/1991 |
| JP | 405043560 A | * | 2/1993 |
| JP | 1993 043560 | * | 2/1993 |
| JP | 06 157422 | * | 6/1994 |
| JP | 407041467 A | * | 2/1995 |
| JP | O7 041467 | * | 10/1995 |
| JP | 11 140030 | * | 5/1999 |
| JP | 2000 191528 | * | 7/2000 |

OTHER PUBLICATIONS

"Glycopeptide Synthesis by and alpha–Amino Acid N–carboxyanhydride (NCA) Method: Ring opening Polymerization of a Sugar–substituted NCA", Macromolecules, 1994, 27, pp. 875–877.*
Reflections, JBC Centennial 1905–2005 100 Years of Biochemistry and Molecular Biology, "From Proteins and Protein Models to Their Use in Immunology and Immunotherapy", published JBC Papers in Press, Sep. 17, 2003, pp. 48507–48519, Michael Sela.*

* cited by examiner

*Primary Examiner*—P. Hampton Hightower
(74) *Attorney, Agent, or Firm*—Oblon, Spivak, McClelland, Maier & Neustadt, P.C.

(57) ABSTRACT

A method of manufacturing a new N-carboxyamino acid anhydride and polyamino acid using a simple process operation.

The method for manufacturing N-carboxyamino acid anhydride comprising reacting α-amino acid with di-tert-butyltricarbonate. The method for manufacturing polyamino acid comprising decarboxylating the N-carboxyamino acid anhydride obtained by reacting α-amino acid with di-tert-butyltricarbonate.

10 Claims, 2 Drawing Sheets

METHOD OF MANUFACTURING N-CARBOXYAMINO ACID ANHYDRIDE AND POLYAMINO ACID

BACKGROUND OF THE INVENTION

1. Field of the Invention

The present invention pertains to a method of manufacturing N-carboxyamino acid and polyamino acid.

2. Description of the Background Art

In recent years, the application of polyamino acids as functional high polymers for fiber materials, liquid crystal materials, optically active materials, and biocompatible materials, for example, in various fields has been anticipated.

As a method of manufacturing these polyamino acids, condensation polymerization of N-carboxyamino acid anhydride (NCA) is commonly known.

N-carboxyamino acid is normally obtained from the reaction of α-amino acid with carbonyl chloride. A problem exists concerning handling of toxic carbonyl chloride. Another problem is difficulty in processing hydrogen chloride gas produced during the reaction process.

The present invention has been completed as a result of extensive research on the synthesis of N-carboxyamino acid anhydride with an object of providing a new method for manufacturing N-carboxyamino acid anhydride using a simple processing operation.

Another object of the present invention is to provide a method for manufacturing polyamino acid using a simple processing operation.

SUMMARY OF THE INVENTION

The method of manufacturing N-carboxyamino acid anhydride of the present invention comprises reacting α-amino acid with di-tert-butyltricarbonate.

The method of manufacturing polyamino acid of the present invention comprises decarboxylating the N-carboxyamino acid anhydride obtained by reacting α-amino acid with di-tert-butyltricarbonate.

Other objects, features and advantages of the invention will hereinafter become more readily apparent from the following description.

DETAILED DESCRIPTION OF THE INVENTION AND PREFERRED EMBODIMENTS

Figure 1:
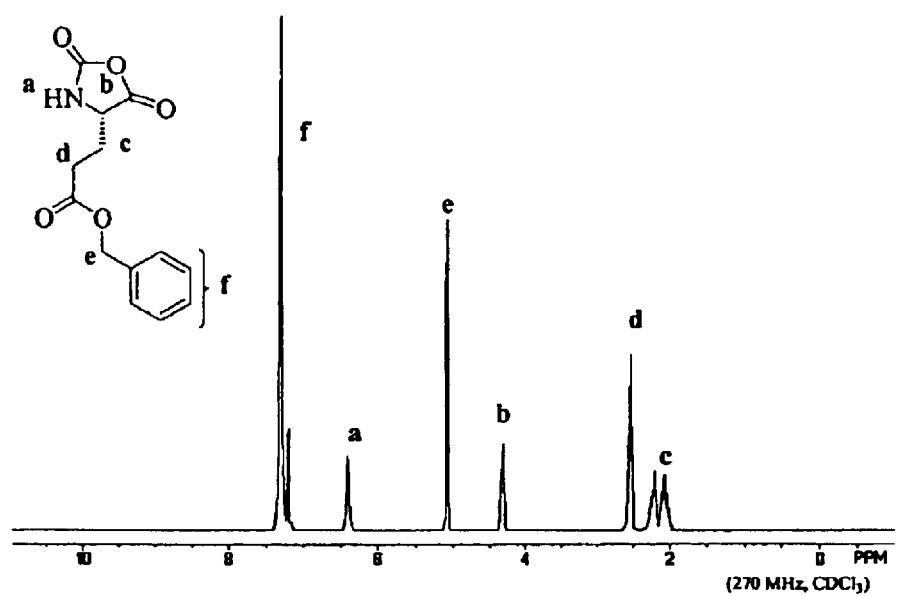
FIG. 1 shows the $^1$H-NMR spectrum of the N-carboxyamino acid anhydride of Example 1.

The present invention will now be described in detail.

In the present invention, N-carboxyamino acid anhydride is manufactured by reacting α-amino acid with di-tert-butyltricarbonate.

The following reaction formula (1) shows the reaction of α-amino acid and di-tert-butyltricarbonate of the manufacturing method in the present invention.

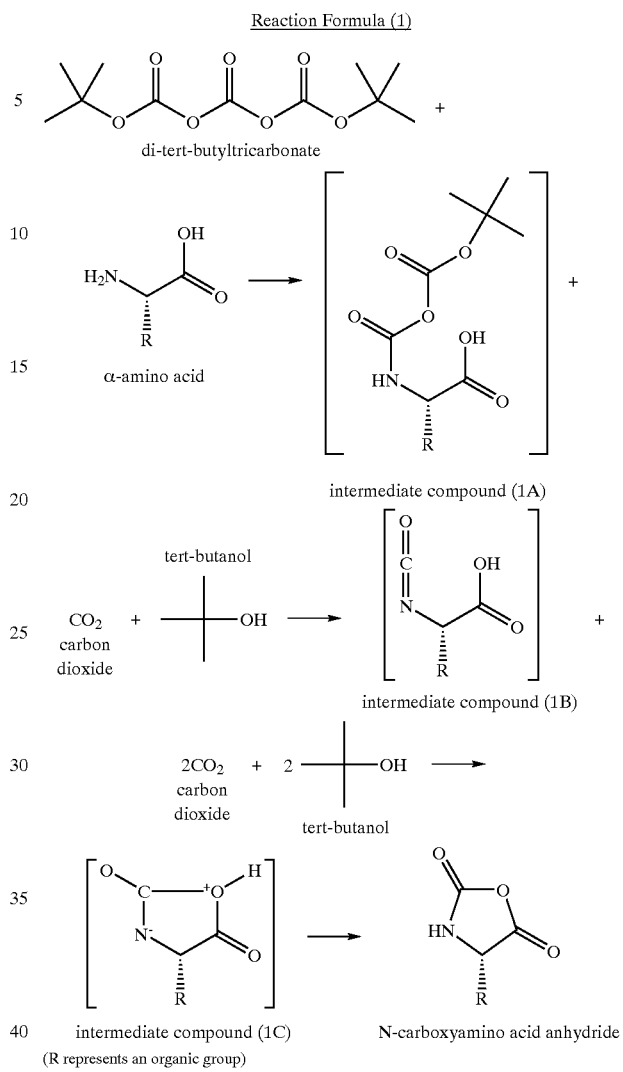

Reaction Formula (1)

(R represents an organic group)

In this reaction, if the α-amino acid and di-tert-butyltricarbonate are reacted in a solvent, tetrahydrofuran for example, bond dissociation of one of the hydrogen atoms bonded to the nitrogen atom of the α-amino acid and a tert-butyl/carbonyl composite group of the di-tert-butyltricarbonate occurs. As a result, carbon dioxide and butanol are produced as by-products, yielding an intermediate compound (1A). Moreover, an intermediate compound (1B) possessing an isocyanate structure can be obtained by bond dissociation of the tert-butyl/carbonyl composite group of the intermediate compound (1A). In the reaction path from the intermediate compound (1A) to the intermediate compound (1B), the bond dissociated tert-butyl/carbonyl composite group produces carbon dioxide and butanol as by-products. Then, N-carboxyamino acid anhydride is formed via an intermediate compound (1C) by cyclizing the intermediate compound (1B).

In this reaction process, an equivalent molar ratio of the starting materials di-tert-butyl tricarbonate and α-amino acid is preferable.

As the solvent, tetrahydrofuran, chloroform, methylene chloride, acetonitrile, and the like may be used.

For the amount of solvent used, 10–20 ml for each 1 mmol of α-amino acid and di-tert-butyl tricarbonate is preferable.

A reaction temperature of 60–80° C. and a reaction time of 30 minutes to 8 hours are preferable.

In this reaction process, the reaction solvent is heterogeneous at initiation of the reaction but becomes homogeneous during progress of the reaction.

The reaction solution is concentrated using a rotary evaporator, then the residue is reprecipitated from hexane and recrystallized from tetrahydrofuran/n-hexane.

According to the method of the present invention, the reaction of α-amino acid and di-tert-butyltricarbonate produces the target N-carboxyamino acid anhydride, and the by-products carbon dioxide and tert-butanol are produced. Since processing of these by-products is comparatively easy, N-carboxyamino acid anhydride can be obtained by an advantageously simple processing operation.

Then, polyamino acid can be obtained by polycondensation involving decarboxylation of the N-carboxyamino acid anhydride obtained by this manufacturing method.

The α-amino acid with the formula shown as the starting material in the Reaction Formula (1) is used in the present invention. As specific examples, a large range of amino acids such as L-alanine, L-leucine, L-phenyl alanine, γ-benzyl-L-glutamic acids and the like can be given.

Of these α-amino acids, γ-benzyl-L-glutamic acid is preferable.

EXAMPLES

The present invention will now be described in detail by way of examples, which should not be construed as limiting the present invention.

In the description of the characteristics of the products in the following examples, $^1$H-NMR and $^{12}$C-NMR indicate the proton nuclear magnetic resonance spectrum and the carbon-13 nuclear magnetic resonance spectrum, respectively, and IR indicates the infrared radiation absorption spectrum. $CDCl_3$ indicates deutriochloroform. In the proton nuclear magnetic resonance spectrum data, s and m shown in parenthesis indicate singlet and multiplet, respectively, and 1H, 2H, 5H, and 9H indicate 1, 2, 5, and 9 equivalents of spectrum strength, respectively.

Example 1

(Synthesis of di-tert-butyltricarbonate)

300 ml of dry tetrahydrofuran was added to 22.7 g (202.3 mmol) of potassium tert-butoxide. After bubbling in carbon dioxide at 0° C., a solution of 10.1 g(33.7 mmol) of tricarbonyl chloride in 50 ml of tetrahydrofuran was added dropwise to the solution and the mixture was allowed to react for 12 hours at room temperature. Next, the obtained reaction solution was concentrated, n-hexane was added to the residue to remove the insoluble matter (potassium chloride) by filtration, and the filtrate was concentrated. The residue was recrystallized to obtain a reaction product at a yield of 38%.

The obtained reaction product was confirmed as di-tert-butyltricarbonate by NMR measurement. The results of NMR measurement are as follows:

$^1$H-NMR($CDCl_3$):δ=1.56(s, 9H, —OC($CH_3$)$_3$)ppm.
$^{13}$C-NMR($CDCl_3$):δ=27.49, 87.5, 143.7, 145.0 ppm.

(Synthesis of N-carboxyamino acid anhydride)

0.5 g (1.9 mmol) of di-tert-butyl tricarbonate was dissolved in 38 ml of the tetrahydrofuran, 0.45 g (1.9 mol) of γ-benzyl-L-glutamine acid was added to this solution and the mixture was allowed to react for 5 hours at 60° C. Then, the resulting reaction solution was filtered and the filtrate was added to a mixed solution of tetrahydrofuran and N-hexane to form a solid. The mixed solution was subjected to recrystallization processing to obtain a white solid as the reaction product at a yield of 70%.

The reaction product was confirmed to have a melting point of 92–94° C. and to be N-carboxy-α-glutamic acid-γ-benzyl anhydride (NCA-benzyl-L-glutamate) using NMR and IR measurement. The results of the NMR and IR measurement are indicated below.

Figure 2:
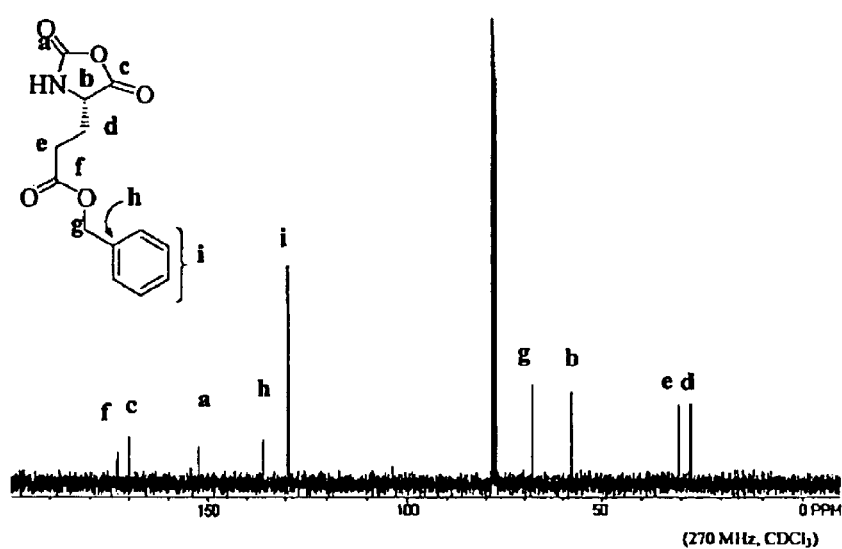
FIG. 2 shows the $^{12}$C-NMR spectrum of the N-carboxyamino acid anhydride of Example 1.

FIGS. 1 and 2 show the nuclear magnetic resonance spectrum obtained by NMR measurement.

$^1$H-NMR($CDCl_3$):δ=2.06–2.24(m, 2H, —CH2), 2.52–2.56 (m, 2H, —$CH_2$), 4.30–4.34(m, 1H, >CH—), 5.08(s, 2H, —O—$CH_2$—), 6.40(s,1H,—NH—), 7.30(s, 5H, —Ph) ppm.
$^{13}$C-NMR(CDCl3):δ=27.5, 30.6, 57.6, 67.8, 129.2, 129.4, 129.5, 135.9, 152.4, 170.2, 173.3 ppm.
IR(KBr):3332.4, 3263.0, 2337.3, 1859.0, 1781.9, 1720.2, 1257.4, 1195.7, 933.4, 740.5 $cm^{-1}$.

The above results confirm that N-carboxy-α-glutamic acid-γ-benzyl anhydride, which is a N-carboxyamino acid anhydride, can be obtained by reacting α-amino acid and di-tert-butyl tricarbonate. Also, it is confirmed that the by-products carbon dioxide and tert-butanol are produced in this method of manufacturing.

Effect of the Invention

N-carboxyamino acid anhydride can be obtained using an easy process operation in the manufacturing method of the present invention, wherein treatment of the starting materials and by-products is comparatively easy.

In the manufacturing method of the present invention, the N-carboxyamino acid anhydride obtained using the above novel method is decarboxylated to produce polyamino acid in a simple manner.

Obviously, numerous modifications and variations of the present invention are possible in light of the above teachings. It is therefore to be understood that, within the scope of the appended claims, the invention may be practiced other than as specifically described herein.

What is claimed is:

1. A method of manufacturing N-carboxyamino acid anhydride comprising reacting α-amino acid with di-tert-butyltricarbonate.

2. A method of manufacturing polyamino acid comprising decarboxylating an N-carboxyamino acid anhydride obtained by reacting α-amino acid with di-tert-butyltricarbonate.

3. The method according to claim 1, wherein said α-amino acid and said di-tert-butyltricarbonate are in an equivalent molar quantity.

4. The method according to claim 1, wherein said reacting is in the presence of a solvent.

5. The method according to claim 1, wherein said α-amino acid is selected from the group consisting of L-alanine, L-leucine, L-phenyl alanine, and α-benzyl-L-glutamic acid.

6. The method according to claim 1, wherein said α-amino acid is α-benzyl-L-glutamic acid.

7. The method according to claim 2, wherein said α-amino acid and said di-tert-butyltricarbonate are in an equivalent molar quantity.

8. The method according to claim 2, wherein said reacting is in the presence of a solvent.

9. The method according to claim 2, wherein said α-amino acid is selected from the group consisting of L-alanine, L-leucine, L-phenyl alanine, and α-benzyl-L-glutamic acid.

10. The method according to claim 2, wherein said α-amino acid is α-benzyl-L-glutamic acid.

* * * * *

UNITED STATES PATENT AND TRADEMARK OFFICE
CERTIFICATE OF CORRECTION

PATENT NO. : 6,762,277 B2
DATED : July 13, 2004
INVENTOR(S) : Kudo et al.

It is certified that error appears in the above-identified patent and that said Letters Patent is hereby corrected as shown below:

Title page,
Items [12] and [75], should read:
-- [12] UNITED STATES PATENT
      Kudo et al.

[75] Inventors: Hiroto Kudo, Yokohama (JP);
                   Takeshi Endo, Yokohama (JP) --

Signed and Sealed this

Twenty-third Day of November, 2004

JON W. DUDAS
*Director of the United States Patent and Trademark Office*